United States Patent [19]

Banucci et al.

[11] 4,225,528
[45] Sep. 30, 1980

[54] MANGANESE COMPLEXES OF PHENYL BENZOIN IN OXIME CATALYSTS

[75] Inventors: Eugene G. Banucci, Scotia; Walter K. Olander, Clifton Park, both of N.Y.

[73] Assignee: General Electric Company, Pittsfield, Mass.

[21] Appl. No.: 880,136

[22] Filed: Feb. 22, 1978

Related U.S. Application Data

[62] Division of Ser. No. 753,507, Dec. 21, 1976, Pat. No. 4,093,598.

[51] Int. Cl.$^2$ .............................................. C07F 13/00
[52] U.S. Cl. .............................. 260/429 J; 260/429 C
[58] Field of Search ......................... 260/429 C, 429 J

[56] References Cited

U.S. PATENT DOCUMENTS

| | | | |
|---|---|---|---|
| 2,116,913 | 5/1938 | Schmidt et al. | 260/429 J |
| 3,248,410 | 4/1966 | Berenbaum | 260/429 J |

*Primary Examiner*—Lester L. Lee
*Attorney, Agent, or Firm*—Morgan, Finnegan, Pine, Foley & Lee

[57] ABSTRACT

This invention provides a novel process for the oxidative coupling of phenolic monomers with novel manganese complexes of phenyl benzoin oximes.

1 Claim, No Drawings

MANGANESE COMPLEXES OF PHENYL BENZOIN IN OXIME CATALYSTS

This is a division, of application Ser. No. 753,507 filed Dec. 21, 1976, now U.S. Pat. No. 4,093,598.

A novel process has been invented for the oxidative coupling of phenolic monomers which is based on the use of novel manganese complexes of phenyl benzoin oximes.

BACKGROUND OF THE INVENTION

The polyphenylene oxides and methods for their preparation are known in the art and are described in numerous publications, including Hay, U.S. Pat. Nos. 3,306,874 and 3,306,875. The Hay processes are based on the use of copperamine complexes. Manganese catalyzed methods for the preparation of polyphenylene oxides are disclosed in McNelis, U.S. Pat. No. 3,220,979; Olander, U.S. Pat. No. 3,956,242; Nakashio, U.S. Pat. No. 3,573,257; and Nakashio, 3,787,361.

In copending applications, Ser. No. 491,370, filed July 24, 1974, now U.S. Pat. No. 3,956,242; Ser. No. 534,903, now U.S. Pat. No. 3,965,069 and Ser. No. 651,682, now U.S. Pat. No. 4,097,462, there are disclosed various procedures for preparing polyphenylene oxides by the oxidative coupling of phenolic monomers. All of these patents and applications are hereby incorporated by reference.

The prior art has employed ω-hydroxy oxime catalysts. The prior art types of ω-hydroxy oxime catalysts have been operable within a restrictive temperature range that precludes economic and practical operation of the processes at temperatures above 95° F.

The optimum temperature range for most prior art manganese chelate catalysts is between 70°–85° F. Achieving this optimum temperature range is not practical in the type of commercial equipment usually employed in the preparation of polyphenylene oxides due to the inherent heat exchange limitations. Alternative methods of exotherm control such as slow monomer addition, oxygen limitation etc., are necessitated to permit operation below 90° F. At temperatures above 95° F., increasing the concentrations of manganese complexes such as the benzoin oxime manganese complexes fails to provide a process that will make high molecular weight polymer.

Catalyst deactivation is known to occur by several modes including in the case of manganese complexes of benzoin oximes base hydrolysis and/or isomerization of α-benzoin oxime to the inactive β-isomer. The latter may accompany catalyst oxidation, but both deactivation mechanisms are thought to be accelerated at the higher temperatures. In addition, the interaction of molecular oxygen with the catalyst, perhaps forming an oxygen adduct, is generally more favored at lower temperatures.

The applicants have discovered that manganese complexes formed from phenyl benzoin oxime are more thermally stable and have an upper temperature limit that is 20° to 25° F. higher than a manganese complex of an ω-benzoin oxime at catalyst ratios of 1250:1 to 1500:1.

Accordingly, it is a primary object of this invention to provide a process for the preparation of a polyphenylene oxide that utilizes a manganese complex catalyst that has a relatively high thermal stability.

It is a further object of this invention to provide a process for the preparation of a polyphenylene oxide that utilizes a manganese complex of phenyl benzoin oxime.

DETAILED DESCRIPTION OF THE INVENTION

The present invention provides a method for the preparation of a polyphenylene oxide which comprises oxidatively coupling a phenolic monomer under polymer forming conditions in the presence of a catalytic amount of a compound of Formula I:

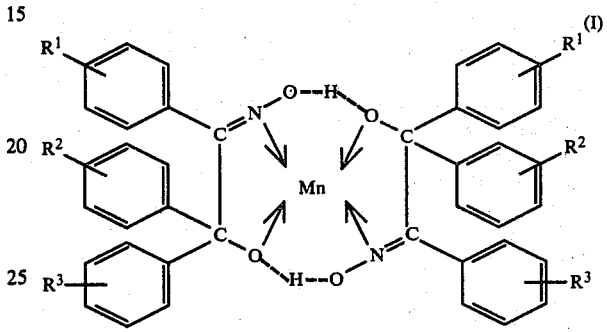

wherein $R^1$, $R^2$ and $R^3$ are independently selected from the group consisting of hydrogen, lower alkyl of from 1 to 8 carbon atoms, aryl, amino, lower alkoxy of from 1 to 8 carbon atoms and halogen. The preferred compounds are those wherein $R^1$, $R^2$ and $R^3$ are hydrogen.

As used herein and in the appended claims, the term lower alkyl of from 1 to 8 carbon atoms is used to include straight and branched claim groups such as methyl, ethyl, i-propyl, propyl, n-butyl, n-hexyl and the like. The term aryl is used to include phenyl and naphthyl. The term lower alkoxy of from 1 to 8 carbon atoms is employed to include methoxy, ethoxy, propoxy, butoxy, hexoxy and the like. Halogen is used to include chlorine, bromine, fluorine and iodine.

The phenyl benzoin oxime complexes may be prepared by combining stoichiometric amounts of a manganese compound and the phenyl benzoin oxime in a suitable solvent such as methanol. Generally it is preferred to employ a 2:1 molar ratio of phenyl benzoin oxime to manganese ion to form a compound of Formula I although less than a ratio of 2:1 e.g. 1:1 these materials will form a catalytically active species. The suitable manganese compounds include the manganese (II) halides such as manganese (II) chloride (also known as manganous chloride) manganese (II) bromide, manganese (II) iodide, etc., as well as other manganese (II) compounds, such as manganese carbonate, manganese (II) oxalate, manganese (II) sulfate, manganese (II) nitrate, manganese (II) phosphates, etc., including hydrated forms thereof. Manganese (VII) compounds such as potassium permanganate may also be employed.

In the practice of the process of the invention, it is contemplated that a mole ratio of from 100:1 to 5000:1, and more preferably a mole ratio of 100:1 to 1500:1 of phenolic monomer to manganese ion, will be employed.

The phenolic monomer may be selected from compounds of the formula:

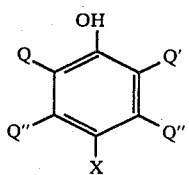

wherein X is a substituent selected from the group consisting of hydrogen, chlorine, bromine and iodine; Q is a monovalent substituent selected from the group consisting of hydrocarbon radicals, halohydrocarbon radicals having at least two carbon atoms between the halogen atom and the phenol nucleus, hydrocarbonoxy and halohydrocarbonoxy radicals having at least two carbon atoms between the halogen atom and the phenol nucleus; and Q' is as defined for Q, and in addition may be halogen and Q" are each as defined for Q' and in addition hydrogen with the proviso that Q, Q' and Q" are all free of a tertiary carbon atom.

The preferred phenolic monomer is 2,6-xylenol.

In general, the reaction temperature employed in the preparation of a polyphenylene oxide in the presence of the manganese phenyl benzoin complex may vary from about 0° to about 125° F. It is preferred to carry out the polymerization at a temperature in the range of from about 95° to about 105° F. The polymerization may be carried out at superatmospheric pressures, e.g., 1 to 40 psig, 1-200 to 1000 psig or even higher pressures. If the self-condensation reaction is discontinued or interrupted due to deactivation of the manganese complex catalyst at elevated temperatures, the reaction can be resumed in a normal fashion by reducing the temperatures of the reaction medium and adding thereto additional manganese chelate catalyst in the amounts required to initiate and maintain the desired catalyst efficiency.

If desired, a secondary amine of the formula

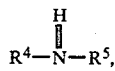

wherein $R^4$ and $R^5$ are lower alkyl of from 1 to 8 carbon atoms, is added to the reaction mixture in an amount that is insufficient to promote the reaction. In general the quantity of the amine employed in the practice of the invention may vary widely. The preferred mole ratio of amine to phenol will be in the range of from about 0.05:100 to about 2.0:100.

The polymerization reaction is carried out by passing a stream of oxygen into the reactor at a rate that is adequate to provide sufficient oxygen to be in excess over that which is absorbed while vigorously stirring the solution. The manganese chelate catalyst solution is then added to a first part of the phenolic monomer solution. The reaction must be carried out in a basic reaction medium, such as that which is provided by a strong alkali metal base, e.g. alkali metal hydroxides, alkali metal alkoxides, etc., or mixtures thereof. Commercially available alkali metal bases which are readily attainable are preferred, such as sodium hydroxide, potassium hydroxide, lithium hydroxide, sodium methoxide, etc. It is especially preferred that anhydrous sodium hydroxide by employed to provide the strong basic reaction environment essential to the polymerization reaction, however, aqueous solutions, e.g. 50 percent, sodium hydroxide can be employed for convenience. The quantity of alkali metal base that is essential to the polymerization reaction can readily be determined without undue experimentation by those skilled in the art. In general, suitable phenol:alkali metal base mole ratios are within the range of from 1:1 to 100:1, preferably from about 40:1 to about 5:1, and even more preferably from about 20:1 to about 10:1. In the preparation of poly(2,6-dimethyl-1,4-phenylene oxide) a mole ratio of 2,6-xylenol:alkali metal hydroxide mole ratio within the range of from about 14:1 to about 18:1 and more preferably from 16:1.

After initiation of the polymerization reaction, the reaction is regulated by the rate of addition of a second part of the phenol reactant portion from a reservoir so that the temperature does not exceed the operable limit. When a polyphenylene oxide having an intrinsic viscosity of about 0.5 dl/g as measured in chloroform at 30° C., is obtained, the reaction may be terminated by the addition of an antisolvent. The antisolvents are well known and include lower alkanols having 1 to 8 carbon atoms. The preferred antisolvent is methanol.

The antisolvent may be added to the polymerization reaction mixture to precipitate the polyphenylene oxide resin along with the manganese chelate catalyst. The alkali activated manganese chelate catalyst is soluble in the typical organic reaction solvent such as toluene while it is insoluble in the typical antisolvent such as methanol.

In the alternative, the polymerization may be terminated by the addition of an aqueous solution of an acid such as acetic acid or sulfuric acid and the polymer recovered by conventional techniques.

DESCRIPTION OF THE PREFERRED EMBODIMENTS

The following examples illustrate the process of this invention. They are merely illustrative and are not to be construed to limit the invention in any manner whatsoever.

EXAMPLE 1

The manganese chelate of phenyl benzoin oxime was prepared as follows:

Preparation of the phenylbenzoin:

168.18 g (1.0 mole) of benzil in 2 liters of ethyl ether was placed in a 5 liter, three necked round bottomed flask, fitted with a reflux condenser, mechanical stirrer, addition funnel and nitrogen bypass. All of the glassware was flame-dried before use while being flushed with nitrogen. A 3 molar solution in ethyl ether of phenyl magnesium bromide (181.23 g, 1.0 mole) was then placed in the addition funnel and added dropwise to the flask over a period of 1.5 hours. The solution was then refluxed overnight. Hydrolysis of the Grignard complex was then accomplished using a 10% solution of $H_2SO_4$ with the concurrent addition of 1.5 liters of $CHCl_3$. After complete hydrolysis, the organic layer was separated and washed with one liter of water. The organic layer was dried with magnesium sulfate, concentrated and recrystallized with hexane to give phenylbenzoin (m.p. 87°–88°, lit 88° C.) of 99% purity in yield of 62%.

Preparation of the Phenylbenzoin oxime:

180 g (0.625 mole) of phenylbenzoin was added to a 3 liter, one necked, round bottomed flask fitted with a reflux condenser and a nitrogen bypass. 1.45 liters of methanol was added to dissolve the phenylbenzoin and free hydroxylamine was prepared by treating 177.9 g. (2.56 moles) hydroxylamine hydrochloride with 209.9 g (2.56 moles) of sodium acetate in water. The resultant solution was added to the phenylbenzoin and the reaction mixture was stirred for 48 hours at reflux at which time an additional 1.24 moles of hydroxylamine was added. The solution was cooled and filtered. The solids were then placed in a Soxhlet extractor and treated with refluxing hexane. After 72 hours the solid remaining in the extraction thimble was collected to yield 40% of the theoretical yield of pure alpha-phenylbenzoin oxime, m.p. 150°–52° C. (lit. 153.5) The hexane extract can be concentrated to yield unreacted phenylbenzoin (50% of theory) which may be recycled to afford additional phenylbenzoin oxime. This material was employed to polymerize 2,6-xylenol using the following composition:

2,6-xylenol—600 g
toluene (reagent)—2040 g
methanol—360 g
sodium hydroxide—24.0 (50% aq)
di-n-butylamine—9.0 g
water—17.6 g
$MnCl_2$—0.41 g
phenylbenzoin oxime—1.98 g The 2,6-xylenol is dissolved in about 1.2 liters toluene and about one-sixth of the resulting solution is transferred to the reactor. Additional toluene, methanol and sodium hydroxide are added to the reactor and the solution is agitated at 1000 rpm. The phenylbenzoin oxime and the $MnCl_2$ are combined in methanol and are added to the reactor five minutes after oxygen flow into the reactor is initiated. Oxygen is supplied at a constant rate of 3.0 SCFH during the polymerization and the remaining 2,6-xylenol solution is added uniformly over a 40 minute period following initiation of the polymerization. The reaction temperature was maintained at 110° F. isothermally through the reaction. The intrinsic viscosity was 0.35 dl/g at 65 minutes as measured in chloroform at 30° C. and 0.41 dl/g at 100 minutes as measured in chloroform at 30° C.

EXAMPLE 2

The general procedure of Example 1 was followed using the following materials:

2,6-xylenol—600 g
toluene—2040 g
methanol—360 g
sodium hydroxide—24.0 g (50% aq)
di-n-butylamine—9.0 g
water—17.5 ml
$MnCl_2$—0.51 g
phenylbenzoin oxime—2.38 g The monomer addition time was shortened from 40 to 30 minutes and the temperature was maintained at 117°–119° F. through 40 minutes and then held at 100° F. during the build. After 90 minutes, the reaction was terminated and the poly(2,6-dimethyl-1,4-phenylene oxide) was found to have an intrinsic viscosity of 0.41 dl/g as measured in chloroform at 30° C.

EXAMPLE 3

The general procedure of Example 1 was repeated with the following materials:

2,6-xylenol—600 g
toluene—1980 g
methanol—420 g
sodium hydroxide—24.0 g (50% aq)
di-n-butylamine—9.0 g
water—17.5 g
manganese chloride—0.51 g
phenylbenzoin oxime—2.38 g During the initial 40 minutes of the reaction, the temperature was maintained between 113°–115° F. and thereafter the temperature was reduced to 95°–100° F. for the duration of the run. The intrinsic viscosity of the poly(2,6-dimethyl-1,4-phenylene oxide) was 0.35 dl/g at 50 minutes as measured in chloroform at 30° C. and 0.51 dl/g at 115 minutes as measured in chloroform at 30° C.

COMPARATIVE EXAMPLE 1

A series of four identical polymerizations were run according to the general procedure of Example 1 using the following materials:

2,6-xylenol—600 g
toluene (containing 2.5–2.7 wt. percent di-n-butylamine)—2040 g
methanol—360 g
$MnCl_2$—0.42 g
benzoin oxime—1.54 g The reaction temperature was maintained as indicated in Table I for 55 minutes of which time the temperatures were adjusted to 85° F. for the remainder of the polymerization. As shown in Table I, catalyst activity is severely impaired above 95° F. This is the case even though sufficient active catalyst is present. Prolonged exposure at 95° F. beyond 55 minutes would have further reduced the polymerization rate.

TABLE I

| | Exotherm Temp °F. | Hydroxyl[a] absorb at $3610^{cm-1}$ | I.V.[b]/Time | | |
|---|---|---|---|---|---|
| | | | 70 | 90 | 110 |
| A | 75 | .341 | 0.64 | 0.68 | — |
| B | 85 | .225 | 0.57 | 0.62 | — |
| C | 95 | .190 | 0.20 | 0.33 | 0.44 |
| D | 105 | .215 | 0.10 | 0.12 | 0.14 | a. The phenolic hydroxyl content was determined after 30 minutes on a reaction aliquot which was extracted with an equal volume of aqueous acetic acid and decanted. A portion of this neutralized polymer was diluted 1:50 in toluene and the hydroxyl absorbance was measured using a Beckman DK-2A spectrophotometer. Slower intermediate reaction rates and less catalyst deactivation occurs at lower temperatures. b. Intrinsic viscosity as measured in chloroform at 30° C.

COMPARATIVE EXAMPLE 2

The general procedure of comparative Example 1 was repeated except that the ratio of 2,6-xylenol to Mn was 750:1 instead of 1500:1. The reaction mixture was as follows:

2,6-xylenol—600 g
toluene—2040 g
methanol—360 g
sodium hydroxide—24 g (50% aq)
di-n-butylamine—9.0 g
water—17.6 g
$MnCl_2$—0.84 g
benzoin oxime—3.10 g The catalyst addition schedule and the temperature profile for the two runs made using this stoichiometry are given in Table II:

TABLE II

| | Temp Profile °F. | | Catalyst | I.V b/time | |
|---|---|---|---|---|---|
| | Exotherm | Build | Addition (min) | 65 | 100 |
| E | 100–105 | 85[a] | 100% at 0 | 0.30 | 0.34 |
| F | 105 | 105 | 50% at 0 50% at 65 | 0.35 | 0.37 | a. After sixty minutes, the temperature is adjusted to 85° F. for the remainder of the reaction. b. Intrinsic viscosity as measured in chloroform at 30° C.

Comparative Example 2 demonstrates that the manganese benzoin oxime catalyst fails to product molding grade poly(2,6-dimethyl-1,4-phenylene oxide) at 100°–105° F. even when employed at twice the normal catalyst level.

Although the above examples have shown various modifications of the present invention, other variations are possible in light of the above teachings. It is, therefore, to be understood that changes may be made in the particular embodiments of the invention described which are within the full intended scope of the invention as defined by the appended claims.

We claim:

1. A manganese complex of the formula:

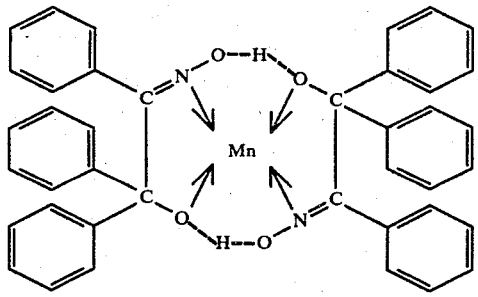

UNITED STATES PATENT AND TRADEMARK OFFICE
CERTIFICATE OF CORRECTION

PATENT NO. : 4,225,528
DATED : September 30, 1980
INVENTOR(S) : Eugene G. Banucci and Walter K. Olander It is certified that error appears in the above—identified patent and that said Letters Patent is hereby corrected as shown below:

In Column 7, line 13 "product" should be --produce--.

Signed and Sealed this

Eighteenth Day of August 1981

[SEAL]

Attest:

GERALD J. MOSSINGHOFF

Attesting Officer  Commissioner of Patents and Trademarks